(12) United States Patent
Bhaskaran et al.

(10) Patent No.: US 8,288,364 B2
(45) Date of Patent: Oct. 16, 2012

(54) BOTANICALLY DERIVED COMPOSITION AND A PROCESS THEREOF

(75) Inventors: Sunil Bhaskaran, Maharashtra (IN); Mohan Vishwaraman, Maharashtra (IN)

(73) Assignee: Indus Biotech Private Limited, Pune, Maharashtra (IN)

( * ) Notice: Subject to any disclaimer, the term of this patent is extended or adjusted under 35 U.S.C. 154(b) by 695 days.

(21) Appl. No.: 12/117,967

(22) Filed: May 9, 2008

(65) Prior Publication Data

US 2009/0281057 A1    Nov. 12, 2009

(51) Int. Cl.
*A61K 31/715*    (2006.01)
(52) U.S. Cl. .......... 514/61; 514/54; 536/123.1; 536/124
(58) Field of Classification Search ................ 514/54, 514/61; 536/123.1, 124
See application file for complete search history.

(56) References Cited

U.S. PATENT DOCUMENTS

| | | | |
|---|---|---|---|
| 5,847,109 | A | 12/1998 | Garti |
| 7,141,254 | B2 | 11/2006 | Bhaskaran |
| 2007/0098763 | A1 | 5/2007 | Sinnott |
| 2008/0027024 | A1 | 1/2008 | Gahler |

*Primary Examiner* — Shaojia Anna Jiang
*Assistant Examiner* — Michael C Henry
(74) *Attorney, Agent, or Firm* — Harness, Dickey & Pierce, PLC (57) ABSTRACT

The present invention relates to a novel botanical compound as provided in structural formula I optionally along with excipients for improving body composition and the factors related to the pre-diabetic and diabetic conditions. It also relates to a process of manufacture of the novel botanical compound for improving body composition and factors related to the pre-diabetic and diabetic conditions. The present invention also relates to the use of the novel botanical compound for improving body composition, reducing body fat, increasing muscle mass, enhancing strength and improving impaired glucose metabolism. The present invention also relates to the use of the novel botanical compound for the improvement of factors related to the pre-diabetic and diabetic conditions.

30 Claims, 6 Drawing Sheets

BOTANICALLY DERIVED COMPOSITION AND A PROCESS THEREOF

FIELD

The present disclosure relates to a novel botanically derived compound with a unique characteristic of improving body composition, increasing lean muscle mass, burning fat, increasing strength and improving glucose metabolism.

The present invention also relates to the use of this compound in subjects who are diagnosed with diabetes and subjects who exhibit the pre-diabetic condition. The present invention also relates to the use of this compound for reducing body fat, increasing lean muscle mass and improving body composition. This improvement in body composition also improves glucose metabolism. The present invention relates to the use of the compound in subjects whose glucose metabolism is impaired. The present invention also relates to the use of the compound to increase muscle mass and enhance strength of the subject.

The present invention also relates to a method of preparation of the compound for improving body composition, increasing lean muscle mass, burning fat, increasing strength and improving glucose metabolism.

BACKGROUND

Diabetes mellitus is an endocrine disorder, which affected 171 million people in the year 2000, and will affect 366 million by the year 2030. This disease is characterized by the defective regulation of blood glucose levels. These levels are regulated by a hormone, Insulin, which is secreted by the beta cells of the Islets of Langerhans in the pancreas. A defective secretion of insulin by the pancreas or resistance to the secreted insulin (insulin resistance) is the main cause of TYPE 2 diabetes mellitus. Defective insulin production is caused by the complex interaction of existing genetic factors with the environmental and life-style choices. In the current cosmopolitan society, life-style choices like obesity, inactivity, and indiscriminate consumption of "energy rich and nutrient lean" processed, frozen or 'ready to eat' foods coupled with prevailing conditions of obesity play a major role in increasing the occurrence of diabetes.

In a healthy body, glucose is effectively regulated by insulin via a closely monitored feedback pathway between the blood glucose levels and the pancreatic hormones. In a diabetic body, the blood glucose levels are on the rise since the defective pancreatic beta cells are not secreting the required amount of insulin. A mal regulation of glucose, which is the primary source of energy for metabolic processes and other cellular functions, causes various metabolic disorders, which are the long-term chronic conditions caused by the onset of diabetes. After the onset of Type 2 Diabetes mellitus, a number of chronic complications develop which affect multiple organs and are responsible for the morbidity and the mortality associated with the disease. Thus, the early diagnosis and immediate management of blood glucose levels is of great importance in the management of diabetes.

Diabetes affects the way the body absorbs and utilizes sugar blood sugar. With the same amount of nutrient intake, the body does not have the sufficient quantity of glucose to generate growth and energy. Additionally, there is also a greater level of catabolic activity causing muscle protein loss and negative nitrogen balance in diabetic patients when compared to individuals with normal blood sugar levels.

Hence, managing blood glucose levels should be coupled with an improvement in body composition in order to effectively manage this disease.

Apart from the growing diabetic population, another area of immediate concern is the alarming rate at which the "pre-diabetic" condition is spreading. In the pre-diabetic condition, the body cells gradually and progressively show an increased resistance to insulin. This resistance to an insulin stimulus leads to a situation of above normal blood glucose levels. Medically this state of elevated blood glucose levels is also referred to as Impaired Glucose Tolerance or Impaired Fasting Glucose (IGT/IFG), depending on which test was used to detect it. They exhibit one of these conditions.

Due to this state of elevated blood glucose levels, pre-diabetic individuals will progressively tend toward a diabetic state. Additionally they may already be experiencing the adverse and chronic health effects associated with a diabetic condition. Glucose circulates in the blood instead of being used by the cells for energy and hence blood glucose levels are elevated. For instance, people with pre-diabetes have a 1.5-fold risk of cardiovascular disease when compared to people with normal blood glucose.

Over 41 million adult Americans between the ages of 40 and 74 have pre-diabetes. Pre-diabetes is a precursor to type 2 diabetes. Obesity (body mass index, BMI>30), unhealthy diet and a sedentary lifestyle can lead to pre-diabetes. Obesity is a root cause of Insulin Resistance, which, in turn, is a key factor in the development of reversible Pre-Diabetes.

Pre-diabetes is the state that occurs when a person's blood glucose levels are impaired but this impairment does not qualify to be diagnosed as diabetes since they do not exhibit any of the clinical symptoms of this disease. Usually the pre-diabetic condition is induced by changes in body composition.

Impaired or an infirmity in body composition usually manifests as an increase in fat particularly central obesity. These accumulated fat cells act as hormone storehouses and start secreting cytokines that inhibit insulin sensitivity. This is the start of a condition called insulin resistance that is characterized by high circulating levels of blood glucose and insulin. This elevation in the levels of insulin and glucose in the blood leads to the conversion of glucose into fat storage causing a further increase in fat mass. This is the start of a vicious cycle, wherein fat mass keeps increasing leading to reduced lean muscle mass. Muscle mass is required for promoting glucose uptake. Hence, a reduction in lean muscle mass leads to reduced glucose uptake that further contributes to the already elevated glucose levels.

Elevated levels of circulating blood glucose are responsible for toxicity to the beta cells of the pancreas ("glucotoxicity"). In fact, beta cell dysfunction is initiated at the pre-diabetic stage. Additionally, by the time diabetes is diagnosed as per the criteria set forth by the World Health Organization or the American Diabetic Association, the pre-existing elevated blood glucose levels have already caused about 40-50% of beta cell dysfunction.

The combination of increased fat mass and the elevated blood sugar levels can be summarized as a series of cascading steps which is a cyclic process and starts with impaired body composition leading to increased fat and decreased lean muscle (skeletal) mass which goes on to cause a decreased glucose metabolism (pre-diabetes) and subsequently to the onset of Type 2 diabetes.

Hence, it can be concluded that reducing body fat is an imperative step in preventing/delaying the progression of pre-diabetes to a diabetic condition. Additionally a property of reducing blood glucose levels is an advantage in the management of pre-diabetes.

Additionally, studies have also indicated the role of body fat distribution in IGT ((Impaired Glucose Tolerance) and IFG (Impaired Fasting Glucose). Women with elevated blood glucose levels can be characterised by a higher accumulated, subcutaneous and total fat mass than women with normal blood glucose levels. Hence, the degree of adiposity, morphological and temporal distribution has all been found to be linked to the pre-diabetic condition. Since there is no single solution that addresses all the symptoms of Insulin Resistance or Pre-Diabetes, you must rely on a multi-faceted approach to reversing these conditions.

Currently, the pre-diabetic population is an unaddressed population, and there is a need for not only blood sugar management but also an improvement of body composition to prevent the progression of the condition and prevent other chronic conditions associated with high body fat content. Besides pre-diabetes there are many other conditions associated with an increased level of body fat (obesity) (Related conditions of increased body fat): insulin resistance, adult onset type 2 diabetes, heart disease and stroke, osteoarthritis, metabolic syndrome, polycystic ovary disease, etc.

Diabetes management requires a combination therapy of blood sugar management as well as an improvement in body composition. Additionally, the pre-diabetic population is increasing with the varied lifestyle choices and sedentary pattern that is setting in recent times.

Considering these factors, there is an unmet need for a therapeutically effective solution that is an answer to all these conditions.

*Trigonella foenum graecum:*

Fenugreek (*Trigonella foenum graecum*) is one of the oldest medicinal plants and belongs to the family Fabaceae. This plant is widely grown in the Mediterranean regions, India, North Africa, Europe and China. Fenugreek is used both as herb and spice. Fenugreek seeds are very commonly used in India as a part of staple food grain. Fenugreek leaves are consumed widely in India as green leafy vegetables and are rich source of calcium, iron, beta-carotene and other vitamin. Fenugreek has a long history of therapeutic uses in Ayurvedic and Chinese medicine. Fenugreek has been reported to exhibit medicinal properties such as controlling the blood sugar, lipid lowering effect, reducing inflammation and controlling infection. This botanical is also thought to delay gastric emptying, slow carbohydrate absorption and inhibited glucose absorption.

The chemical composition of fenugreek seeds is Moisture—9%, Ash—3%, Lipids—8%, Protein—26% and Starch—6%. Additionally, fenugreek seeds also have a total fibre content of 48%, a gum content of 20% and a neutral detergent fibre content of 28%.

The therapeutic applications of fenugreek, namely, blood sugar lowering, slow absorption of glucose and carbohydrates, delayed gastric emptying and lipid and cholesterol lowering effects are attributed to the presence of gums in fenugreek seeds. Gums inherently have properties by which they can slow the absorption of molecules during the digestion and excretion process. They also play a role appetite suppression by delaying gastric emptying.

Typically, gums are either hydrophobic or hydrophilic high molecular weight molecules with colloidal properties that in an appropriate solvent or a swelling agent produce gels or highly viscous suspensions or solutions. The ability of gums to absorb appropriate solvents and swell is the main reason for the physiological effect of gum in the digestion process.

Seeds are an ancient source of gums. Most seeds contain starch as their principal food store that is used for the initial growth of the plant. Many seeds contain polysaccharide food reserves other than starch and some of these seeds are harvested to make dietary gums. These dietary polymers or gums are more commonly referred to as dietary fibres.

Gums or dietary fibres occur as linear chain compounds composed of sugar units which are called glycosyl units. Linear chains may have several hundreds of glycosyl units. Some dietary polysaccharides (fibres) occur as branched chain polysaccharides and are referred to as glycans. The molecular weights of both linear and branched chain fibres span a wide range of 2,000 Da-100,000 Da. An important difference between the linear and branched polysaccharides is their contribution to the viscosity of a solution. Linear fibres tend to render a solution more viscous than branched fibres. The viscosity increasing property of linear fibres is due to the mild hydrolytic cleavage of the linear molecule.

The main components which constitute the gum in the fenugreek seeds are galactose and mannose. These sugars link in specified proportions to form linear polysaccharide fibres. These polysaccharide sugars form the endosperm reserve. The gum or fibre obtained from fenugreek is known to be well suited for viscosity building and as a binding agent. Additionally, Fenugreek galactomannan is unique from other galactomannans due to the fact that the mannose galactose ratio is 1:1. In addition, it is more soluble in cold water than its existing counterparts are. Also, the documented evidence of fenugreek derived galactomannan gum or dietary fibre is approximately 30,000 Daltons. The yield obtained by the extraction of these galactomannans has been restricted to 15-20%.

Hence, the physiological functions of fibres are primarily due to their ability to swell in a specific solvent and to increase the viscosity of a given solution. These two properties contribute to delayed gastric emptying and lower levels of absorption of molecules in the presence of fibres.

Dietary fibres are composed of a large number of varying polysaccharides which are not metabolized in the upper digestive tract. Hence, when dietary fibre passes through the stomach into the small and then the large intestine, the swelling and rheology related properties of fibres contribute to their physiological function.

Due to their inherent bulking tendency, they add a significant amount of bulk to the contents as they pass through the gastrointestinal tract. Hence, they decrease the contact of the small and large intestine to the molecules that transit through them and thus lower the absorption of molecules like sugar. Additionally, they also surround the bile secreted in the small intestine and prevent its re-absorption, thereby lowering the availability of bile which is the starting point of cholesterol.

Also, their property to increase viscosity of a medium delays gastric emptying and hence causes appetite suppression.

Hence, it is concluded that these high molecular weight polysaccharides have a peripheral impact on the GIT health. Peripheral impact refers to a location specific action. This action is not systemic since it does not get absorbed into the blood stream. Absorption of these polysaccharides is not possible due to a high molecular weight. Hence, the action on these high molecular weight molecules is limited to the location of their presence.

Prior Art:

United States Patent Application 2008/0027024 refers to a combination of glucomannan, xanthan gum and alginate to produce viscosity so as to deliver a dietary fibre for the use of promoting satiety, promoting weight loss, lowering blood glucose levels, or lowering blood cholesterol levels in a mammal. This patent refers to a combination of different gums so as to achieve the desired viscosity to promote the functions claimed in the document.

US Patent Application 2007/0098763 refers to a composition that consists of glucomannan and at least one galactomannan. In this patent, the glucomannan referred to is derived from the roots or corm of the konjac plant. Also, these polysaccharides consist of glucose and mannose in the ration 5:8. A main point in the glucomannan derived from the konjac plant is that the molecular weight of this glucomannan is the highest of any known fibre and ranges from 200,000-2,000,000 Daltons. Since this is a high molecular weight fiber, it will not be absorbed into the blood stream will hence have only a peripheral action on the body of the subject.

U.S. Pat. No. 5,847,109, refers to a composition containing fenugreek derived galactomannans with at least 50 repeating units. The molecular weight of this claimed compound would be ~18,000 Daltons. This is a high molecular weight compound. Since this is a high molecular weight compound, it will not get absorbed into the blood stream. The effect claimed in this patent related to reduction in post prandial glucose, cholesterol reduction and enhanced insulin response are related to the peripheral action of any dietary fiber. This action is location specific and is generated from the small and large intestines. Since these molecules are of large molecular weights and are gums, they enter the small intestine, absorb the water, swell up and occupy a large part of the lumen of the large intestine thereby preventing the absorption of sugars and the re-absorption of bile to produce cholesterol. This peripheral action of this composition is responsible for it physiological function. This composition cannot get absorbed into the blood stream due to its high molecular weight and hence will not produce a systemic action.

U.S. Pat. No. 7,141,254, relates to a composition for the treatment of diabetes which includes trigonelline, amino acids and galactomannan. Also, the galactomannan referred to in this patent is present in the range of 10-60%. Additionally, there is no data on the effect of galactomannan independent of trigonelline and amino acids.

OBJECTS OF PRESENT INVENTION

The main object of the present invention is to develop a purified novel botanical compound. Another object of the present invention is to improve factors associated with a diabetic and a pre-diabetic condition.

Yet another object of the present invention is to use this purified compound for reduce body fat thereby increasing muscle mass and improving body composition.

Still another object of the present invention is to use the purified compound to maintain healthy blood glucose levels in a subject diagnosed with a diabetic and a pre-diabetic condition. Another object is to delay or prevent the progression of a pre-diabetic condition to type 2 diabetes.

Still another object of the present invention is to use the purified compound to enhance glucose uptake by cells by an insulin-like mechanism.

Still another object of the present invention is to use the purified novel botanical compound to reduce body fat thereby improving body composition and increasing muscle mass.

Still another object of the present invention is to develop a process of preparation of the purified novel botanical compound for improving factors associated with the diabetic, pre-diabetic condition, to reduce body fat thereby improving body composition and increasing muscle mass.

SUMMARY

Accordingly, the present invention provides a compound of structural formula I,

Formula I compositions comprising the compound of structural formula I and pharmaceutically acceptable additive(s) for improving factors associated with pre-diabetic and diabetic conditions. A process for preparation of compound of structural formula I from plant *Trigonella foenum-graecum*, wherein said process comprises steps of: extracting flaked seeds with aliphatic hydrocarbon solvent and hydro-alcohol to remove fatty matter; concentrating the extract to obtain a semi solid mass; dissolving concentrated mass to obtain a clear solution; passing clear solution through ion-exchange resin to remove nitrogenous and ionic bases to obtain a clarified solution; passing the clarified solution through adsorbent column to retain active compounds; and concentrating resultant clear solution followed by drying under vacuum to obtain powder of the compound of formula I is also provided. A method of treating pre-diabetic and diabetic disease conditions in a subject in need thereof is disclosed, said method comprising step of administering pharmaceutically effective amount of compound of structural formula I, optionally along with pharmaceutically acceptable additives to the subject.

DETAILED DESCRIPTION

The present invention is in relation to a compound of structural formula I.

Formula I

In another embodiment of the present invention, said compound is a low molecular weight galactomannan having molecular weight ranging from 200 to 1000 daltons, preferably about 705 daltons.

In yet another embodiment of the present invention said compound is having molecular formula of $C_{24}H_{48}O_{23}$.

Still another embodiment of the present invention said compound is obtained from plant *Trigonella foenum graecum*.

Still another embodiment of the present invention said compound for improves body composition, strength and factors associated with the pre-diabetic and diabetic conditions.

Figure 1:
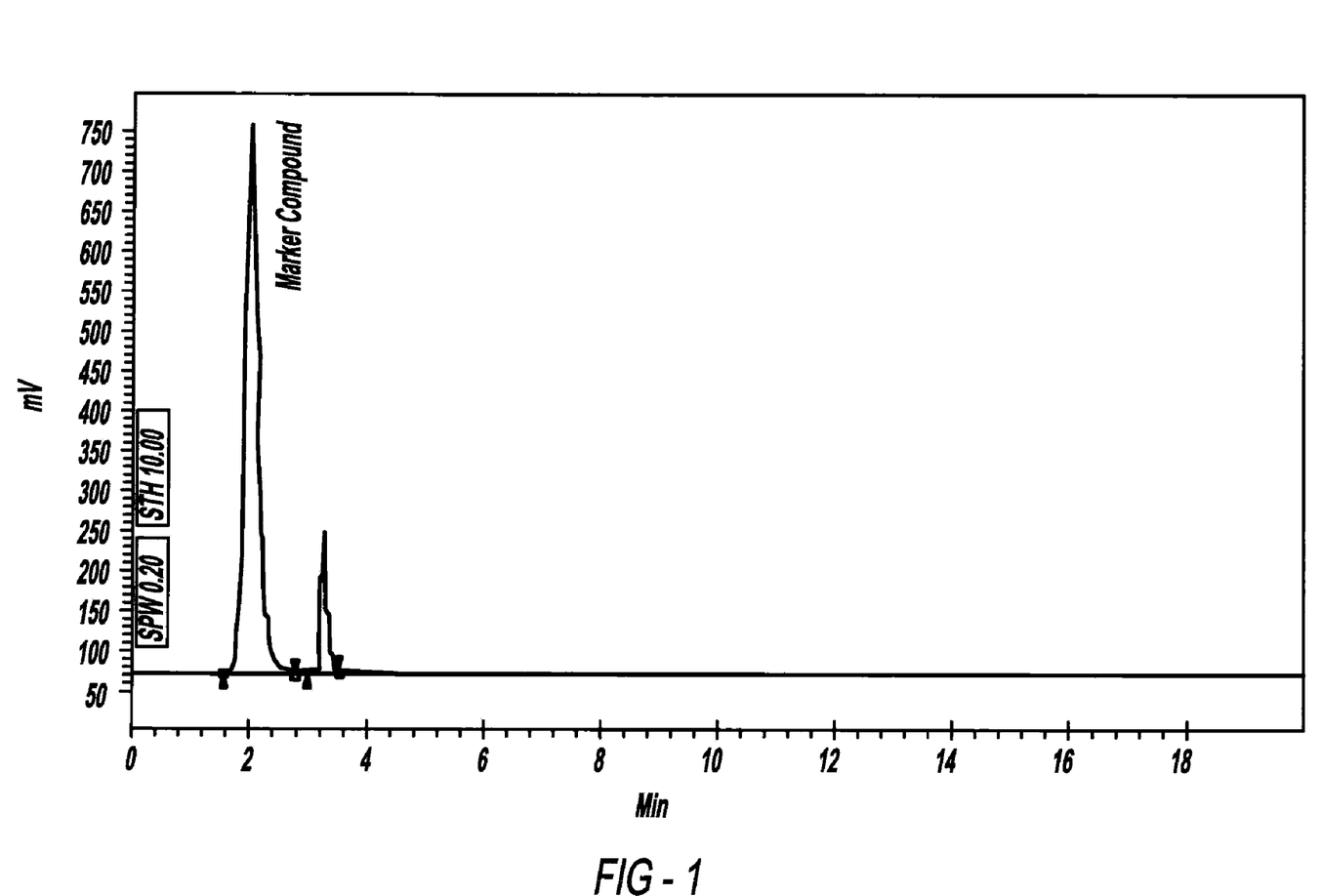
FIG. 1 is a graph depicting HPLC chromatogram of compound of structural formula I.

Still another embodiment of the present invention said compound is provided as HPLC chromatogram in FIG. 1.

Figure 2:
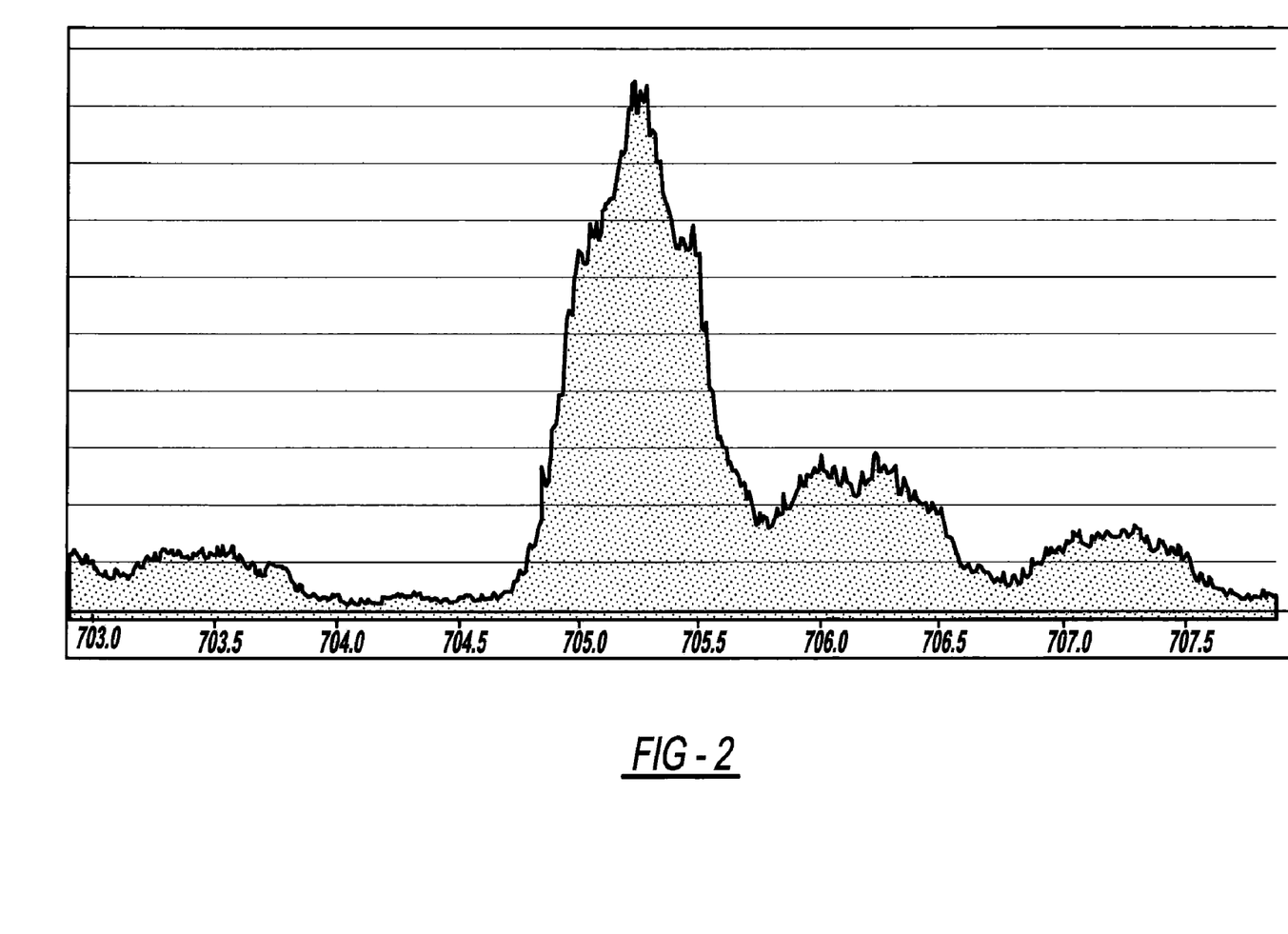
FIG. 2 is a graph depicting LC-MS chromatogram of compound of structural formula I.

Still another embodiment of the present invention said compound is provided as LC-MS chromatogram in FIG. 2.

The present invention also relates to a composition comprising compound of structural formula I optionally along with pharmaceutically acceptable additive(s) for improving body composition, strength and factors associated with pre-diabetic and diabetic conditions.

In another embodiment of the present invention the additives are selected from a group comprising granulating agents, binding agents, lubricating agents, disintegrating agents, sweetening agents, coloring agents, flavoring agents, coating agents, plasticizers, preservatives, suspending agents, emulsifying agents and spheronization agents.

In yet another embodiment of the present invention said composition is formulated into various dosage forms selected from a group comprising tablet, troches, lozenges, aqueous or oily suspensions, dispersible powders or granules, emulsion in hard or soft gel capsules, syrups and elixirs.

Still another embodiment of the present invention said compound is obtained from plant parts of *Trigonella foenum graecum*. Still another embodiment of the present invention said plant parts are selected from a group comprising roots, shoots, leaves, seeds, entire plant and preferably seeds.

Still another embodiment of the present invention said composition is non-toxic and free of side effects.

Still another embodiment of the present invention said pre-diabetic and diabetic conditions comprises poor body composition, lean muscle mass, decreased fat burning, decreased strength, impaired glucose metabolism, increased resistance to insulin, increase in blood glucose, cardiovascular diseases, obesity and type-2 diabetic condition.

The present invention is in relation to a process for preparation of compound of structural formula I from plant *Trigonella foenum-graecum*, wherein said process comprises steps of: extracting flaked seeds with aliphatic hydrocarbon solvent and hydro-alcohol to remove fatty matter; concentrating the extract to obtain a semi solid mass; dissolving concentrated mass to obtain a clear solution; passing clear solution through ion-exchange resin to remove nitrogenous and ionic bases to obtain a clarified solution; passing the clarified solution through adsorbent column to retain active compounds; and concentrating resultant clear solution followed by drying under vacuum to obtain powder of the compound of formula I.

In another embodiment of the present invention, said extraction is carried out for a time period ranging from 3 to 12 hrs and preferably about 10 hrs.

In yet another embodiment of the present invention said extraction is carried out at a temperature ranging from 30 to 40° C. and preferably about 35° C.

Still another embodiment of the present invention said aliphatic hydrocarbon solvent is selected from a group comprising hexane, heptane, octanes and cyclohexanes, preferably hexane.

Still another embodiment of the present invention the hydro alcohol for extraction is in a ratio ranging from 1:9 to 9:1 and preferably about 1:7.

Still another embodiment of the present invention said extract is concentrated under vacuum at a temperature ranging from 45 to 55° C. and preferably about 50° C.

Still another embodiment of the present invention said mass is dissolved in deionized water.

Still another embodiment of the present invention said ion-exchange resin is cation exchange gel type resin.

Still another embodiment of the present invention the yield of the compound of formula I is about 32 gms/1000 gm of fenugreek seeds.

Still another embodiment of the present invention the purity of the compound of formula I is ranging from 90% to 97%, preferably about 95%.

Still another embodiment of the present invention said extract is concentrated under vacuum at a temperature ranging from 50 to 75° C. and preferably about 50° C.

The present invention is in relation to a method of treating pre-diabetic and diabetic disease conditions in a subject in need thereof, said method comprising step of administering pharmaceutically effective amount of compound of structural formula I optionally along with pharmaceutically acceptable additives to the subject.

In another embodiment of the present invention said pre-diabetic and diabetic conditions comprises poor body composition, lean muscle mass, decreased fat burning, decreased strength, impaired glucose metabolism, increased resistance to insulin, increase in blood glucose, cardiovascular diseases, obesity and type-2 diabetic condition.

In yet another embodiment of the present invention said additives are selected from a group comprising granulating agents, binding agents, lubricating agents, disintegrating agents, sweetening agents, coloring agents, flavoring agents, coating agents, plasticizers, preservatives, suspending agents, emulsifying agents and spheronization agents.

Still another embodiment of the present invention said composition is formulated into various dosage forms selected from a group comprising tablet, troches, lozenges, aqueous or oily suspensions, dispersible powders or granules, emulsion in hard or soft gel capsules, syrups and elixirs.

Still another embodiment of the present invention the subject is an animal or human being.

Still another embodiment of the present invention said compound improves pre-diabetic and diabetic conditions such as insulin-like activity, reducing blood sugar levels, preventing wasting of body, improving body composition, reducing body fat and increasing lean muscle mass.

Still another embodiment of the present invention said compound is obtained from plant parts of *Trigonella foenum graecum*. Still another embodiment of the present invention said compound is obtained from plant parts selected from a group comprising roots, shoots, leaves, seeds, entire plant and preferably seeds.

One embodiment of the present invention relates to a botanical compound as characterized in HPLC chromatogram of FIG. 1 optionally along with pharmaceutically acceptable excipients for improving body composition and improving impaired glucose metabolism. Another aspect of the present embodiment is that the compound is derived from botanical sources preferable *Trigonelle foenum graecum*. Another aspect of the present embodiment is that the compound is a low molecular weight compound and has a molecular ranging from 200-1000 Daltons. Another aspect of the present invention is that the compound does not have any androgenic activity.

Another embodiment of the present invention relates to the process of manufacture of a botanical compound provided in HPLC chromatogram of FIG. 1 wherein the process comprises the steps of flaking seeds for size reduction, removal of oils and lipids with an aliphatic hydrocarbon solvent, extraction with an aqueous aliphatic alcoholic solvent, removal of unwanted compounds and concentration and drying to obtain a powder. One aspect of the present embodiment relates to the aliphatic hydrocarbon solvent that is chosen from the group hexanes, heptanes, octanes and cyclohexanes, preferably hexane. Another aspect of the present embodiment relates to the aqueous aliphatic alcoholic solvent for extraction that is chosen from the group methanol, ethanol and isopropanol, preferably ethanol. In another aspect of the present embodiment, the extraction is carried out at a temperature ranging from 30 to 40° C. and preferably 35° C. In another aspect of the present embodiment, the extraction is carried out for a time period ranging from 3 to 10 hrs and preferably 10 hrs. Another aspect of the present embodiments relates to the purity of the botanical compound which ranges from 0-95%.

Another embodiment of the present invention relates to the use of a botanical compound as characterized in HPLC chromatogram of FIG. 1 and compound of structural formula I for improving body composition and impaired glucose metabolism. Another aspect of the present embodiment relates to the use of the compound to reduce body fat and increase muscle mass. Another aspect of the present invention relates to the use of the compound to increase strength. Another aspect of the present invention relates to the use of the compound to improve impaired glucose metabolism.

Another embodiment of the present invention relates to the use of a compound as given in structural formula I and its HPLC chromatogram provided in FIG. 1, to improve factors related to pre-diabetic and diabetic conditions. Another aspect of the present embodiment relates to factors related to the pre-diabetic and diabetic conditions wherein improvement of factors related to pre-diabetic and diabetic condition are selected from the group comprising insulin-like activity, reducing blood sugar levels, improving body composition, reducing body fat, and increasing lean muscle mass.

The present invention relates to a novel botanical compound and its derivatives for improving the factors associated with the diabetic and pre-diabetic condition having the HPLC fingerprint shown in FIG. 1 and is further characterized by LC-MS chromatogram as provided in FIG. 2. The present invention also relates to a method of manufacture of this novel botanical compound by the process illustrated in this document. The present invention relates to the use of the compound to improve body composition by reducing or burning body fat and by increasing muscle mass. The present invention also relates to the use of the compound to increase strength in a subject in need thereof. The present invention also relates to the use of the botanical compound to improve blood sugar and body composition factors associated with a diabetic and a pre-diabetic condition. The present invention also relates to the use of the botanical compound to promote effective body composition management related to the diabetic and a pre-diabetic condition.

In another embodiment of the present invention, the compound of structural formula I has the fingerprint as shown in FIG. 1 and optionally with excipients. In another embodiment of the present invention, the compound is characterized by LC-MS chromatogram as shown in FIG. 2 and optionally with excipients. In another embodiment, the compound is derived from fenugreek seeds is a low molecular weight compound and has a molecular weight of 705 Daltons. In another embodiment of the present invention, the compound has a systemic effect on the body of the subject. In still another embodiment, the present invention relates to the use of a compound to improve body composition by reducing or burning fat and increasing muscle mass. This increase in muscle mass also causes an increase in strength.

In another embodiment, the present invention relates to the use of the compound to drive glucose into cells in an insulin-like manner. In still another embodiment, the present invention relates to the use of the compound to reduce blood sugar levels in a subject in need thereof.

In another embodiment of the present invention, the excipients are selected from a group comprising additives, gums, sweeteners, coatings, binders, disintegrants, lubricants, disintegration agents, suspending agents, solvents, colorants, glidants, anti-adherents, anti-static agents, surfactants, plasticizers, emulsifying agents, flavors, viscosity enhancers and antioxidants.

In still another embodiment of the present invention, the compound is formulated into dosage forms like liquid, powder, capsule, tablet, injectable, patch, ointment, gel, emulsion, cream, lotion, dentifrice, spray and drop. In still another embodiment of the present invention, the compound is either a powder or liquid.

The present invention also relates to a process of preparation of the novel botanical compound, wherein the process comprises steps of:

1) Preparation for extraction: Flaking of fenugreek seeds to reduce the size;
2) Removal of oils and lipids;
3) Extraction with an aqueous alcoholic solvent;
4) Removal of alkaloids, nitrogenous compounds, high molecular weight polar compounds and saponins; and
5) Concentration and drying to obtain a powder.

The present invention also relates to use of the present compound of structural formula I further characterized by the fingerprint provided in FIG. 1 optionally along with excipients to manufacture a medicament for the improvement of factors related to the diabetic and pre-diabetic condition and to the reduce body fat thereby improving body composition and increasing muscle mass. The purity obtained of the botanical compound ranges from 0-95%, preferable 90%

In still another embodiment of the present invention, the compound is either a powder or liquid and has minimal side effects.

In one embodiment of the present invention, the isolation of the compound of structural formula I which is further characterized by the fingerprint in FIG. 1 from fenugreek seeds involves the process as described below:

The compound of FIG. 1 was obtained from different seed materials mainly containing high molecular weight (for example Fenugreek seeds) and low molecular weight water-soluble bioactive compounds. They are isolated in a unique way that allows only the compounds having molecular weights ranging from 1000 to 200 or even below to be extracted. The seeds were flaked using roller flaking machine to size of thickness varying between 1 mm to 8 mm. The effective exposure of the inner core was achieved by flaking to a size preferably of 1 mm thickness. The flaked seeds were packed in an extractor fitted with bottom filter of suitable mesh size preferably 200 mesh so as not to allow the seed meal to flow down along with solvent. An aliphatic hydrocarbon solvent like hexane, heptanes, octane, and cyclohexane, preferably hexane is allowed to percolate through the packed seed layer. The percolated aliphatic hydrocarbon layer is recycled efficiently over period of 10 to 12 hrs so that the resultant seed meal is free of oils & lipids. The aliphatic hydrocarbon solvent extracted meal is re-extracted with a solvent mixture comprising of aqueous aliphatic alcohol in the aqueous to alcohol ratio of 1:1 to 9:1 preferably 1:7 as the solvent. The said alcohol may be methanol, Ethanol, Isopropanol, preferably ethanol as the alcoholic solvent. The aqueous alcohol mixture is passed from top to bottom through the seed layer in the percolater. The process of recycling the solvent was continued for a period of time ranging between 3 hrs to 10 hrs preferably 8 hrs at room temperature.

The clear extract from the bottom of the percolator is inspected visually for any suspended particles, and is re-filtered if necessary. The clear filtrate is vacuum concentrated at temperature ranging between 50° C. to 75° C. preferably at 55° C to a pasty mass. The paste is re-dissolved in deionized water to a clear solution consisting of around 2% solid content. The clear solution is passed through an Ion exchange resin column comprising a strong acid anion exchange resin capable of removing Alkaloids, and other nitrogenous compounds from the stream. The column outlet liquid devoid of basic compounds and other amino acid is passed through an adsorbent column consisting of polymer adsorbent amberlyt XAD-761 that is capable of removing all high molecular weight polar compounds and Saponin from the stream. The outlet liquid was concentrated to 50% solids and spray dried in a co-current spray dryer to obtain a powder.

The entire process of the purified compound isolation consists of the following steps to obtain the said low molecular weight compound which answers for sugars on Thin layer chromatography followed by 10% alcoholic sulphuric acid spray and heating:

1) Seeds (fenugreek) are flaked to expose the inner core so as to ensure effective defatting, extraction and processing.
2) An aliphatic hydrocarbon solvent is passed through the fenugreek bed repeatedly to achieve effective defatting of the seed.
3) The flaked seeds are loaded in a percolator and solvent mixture comprising an aliphatic alcohol and water are passed through the seed layer to achieve effective extraction.
4) The solvent is vacuum concentrated at lower temperatures to ensure the integrity of the input and the resultant mass is dissolved in deionized water to get clear solution.
5) The clear solution thus obtained is passed through an ion exchange column to remove all nitrogenous substances and ionic bases.
6) The clear solution thus obtained is passed through a polymeric adsorbent XAD-761 to retain the Saponins and high molecular weight compounds.
7) The resultant outlet solution is concentrated to 50% solid solution at low temperature.
8) The solution is dried using a vacuum tray dryer or a spray dryer to get a free flowing powder.

Dose of the Product of Instant Invention

Human dose is 1 mg per kg to 100 mg per kg preferably 6.5 mg per kg for fat burning, increase in lean mass, increase in strength and controlling pre-diabetic condition. 2 mg per kg to 100 mg per kg for controlling diabetes, preferably 10 mg per kg for controlling diabetes and recovering weight loss in diabetes.

Animal dose in rat is 10 mg per kg to 200 mg per kg preferable 35 mg per kg for fat burning and lean mass increase and 60 mg per kg for reducing blood sugar in a diabetic condition.

The technology of the instant Application is further elaborated with the help of following examples. However, these examples should not be construed to limit the scope of the invention.

EXAMPLE 1

1000 gms of fenugreek seeds having a moisture content less than 7% were flaked in a roller flaker to a thickness of 5 mm The flaked material is stalked in a column having a bed height of 300 mm. 5 liters of hexane was passed through the layer of fenugreek and the elluent collected from the bottom is recycled through the fenugreek layer for a period of 10 hrs at 35° C. After 10 hrs the fenugreek layer was drained free of hexane. Solvent mixture (8 liters) comprising of Isopropyl alcohol and water in the ratio of 4:1 was passed through the layer for a period of 8 hrs at 35° C. by recycling the elluent. After 8 hrs the fenugreek bed is drained free of extracts and all the collected extracts. The collected extracts were concentrated to semisolid mass under vacuum at 50° C. The concentrated mass is re-dissolved in 5 liters of deionized water to get a clear solution. The clear aqueous solution was passed through a column containing 500 ml of strong acid cation exchange resin in macroporous form slowly over a period of 2 hrs.

The column elluents were checked by TLC screening for the presence of alkaloids and nitrogenous compounds like amino acids. (TLC system Butanol, acetic acid, water in the ratio 12:8:2). Detection was done using Ninhydrin reagent. After completion of the column the outlet liquid was passed through 750 ml of resin bed containing Amberlite XAD-761 over a period of 3 hours. The column remainder which is collected from the outlet is concentrated below 50° C. under vacuum to get thick paste which is spray dried in a small spray drier under following conditions.

Inlet temperature: 160° C.
Outlet temperature: 80° C.
Atomizer RPM: 12000.
Yield 32 gms

EXAMPLE 2

1000 gms of fenugreek seeds having a moisture content less than 7% were flaked in a roller flaker to a thickness of 5 mm The flaked material is stalked in a column having abed height of 300 mm. 5 liters of hexane was passed through the layer of fenugreek and the elluent collected from the bottom is recycled through the fenugreek layer for a period of 10 hrs at 35° C. After 10 hrs the fenugreek layer was drained free of hexane. Solvent mixture (8 liters) comprising of Ethyl alcohol and water in the ratio of 4:1 was passed through the layer for a period of 8 hrs at 35° C. by recycling the elluent. After 8 hrs the fenugreek bed is drained free of extracts and all the collected extracts. The collected extracts were concentrated to semisolid mass under vacuum at 50° C. The concentrated mass is re-dissolved in 5 liters of demonized water to get a clear solution. The clear aqueous solution was passed through a column containing 500 ml of strong acid cation exchange resin in macroporous form slowly over a period of 2 hrs. The column elluent were checked by TLC screening for the presence of alkaloids and nitrogenous substances like amino acids. (TLC system Butanol.acetic acid, water, in the ratio 12:8:2). Detection was done using Ninhydrin reagent. After completion of the column the outlet liquid was passed through 750 ml of resin bed containing Amberlite XAD-761 over a period of 3 hours. The column remainder that is collected from the outlet is concentrated below 50° C. under vacuum to get thick paste that is vacuum dried to get a fine powder.

H.P.L.C of the above compound was carried out using reverse phase column and ELSD detector for detection. The results showed marker 1 major compound (91% area purity) and remaining a minor compound. The HPLC conditions are provided below:

| | |
|---|---|
| CONC. | 100 mg in 50 ml. Methanol |
| DETECTOR | Evaporative Light Scatter. |
| COLUMN | C18. Reverse Phase. 250 × 4.6 mm × 5 Micron |
| FLOW RATE | 1 ml/min. |
| HELIUM | 1.3 ml/min. |

| Index | Name | Start [Min] | Time [Min] | End [Min] | PEAKHEIGHT [μV] | PEAKAREA [μV · sec] | Area % [%] |
|---|---|---|---|---|---|---|---|
| 1 | Marker Compound | 1.593 | 1.975 | 2.822 | 658405.77 | 11435381.23 | 91.750 |
| 2 | UNKNOWN | 3.116 | 3.275 | 3.545 | 174541.71 | 1028220.02 | 8.250 |
| Total | | | | | | | 100.000 |

Similarly, the LC-MS conditions are provided below:

| Type | Start Mass | End Mass | Set Mass |
|---|---|---|---|
| MS Scan | 703 Settings | 708 Readbacks | |
| Source (ES+) | | | |
| Capillary (kV) | 4.00 | 4.01 | |
| Cone (V) | 90.00 | 91.21 | |
| Extractor (V) | 2.00 | 2.32 | |
| RF Lens (V) | 0.3 | 0.3 | |
| Source Temperature (° C.) | 100 | 99 | |
| Desolvation Temperature (° C.) | 150 | 148 | |
| Cone Gas Flow (L/Hr) | 50 | 49 | |
| Desolvation Gas Flow (L/Hr) | 700 | 695 | |
| Analyser | | | |
| LM 1 Resolution | 15.0 | | |
| HM 1 Resolution | 14.9 | | |
| Ion Energy 1 | 1.0 | | |
| Entrance | 50 | −50 | |
| Collision | 2 | −3 | |
| Exit | 50 | −50 | |
| LM 2 Resolution | 15.0 | | |
| HM 2 Resolution | 15.0 | | |
| Ion Energy 2 | 3.0 | | |
| Multiplier (V) | 650 | −650 | |
| Syringe Pump Flow (uL/min) | 20.0 | | |
| Pressure Gauges | | | |
| Gas Cell Pirani Pressure (mbar) | <1e−4 mBars | | |
| MUX Configuration | | | |
| Probe | Standard | | |

EXAMPLE 3

1000 gms of fenugreek seeds having a moisture content less than 7% were flaked in a roller flaker to a thickness of 6 mm. The flaked material is stalked in a column having a bed height of 300 mm. 5 liters of hexane was passed through the layer of fenugreek and the elluent collected from the bottom is recycled through the fenugreek layer for a period of 10 hrs at 35° C. After 10 hrs the fenugreek layer was drained free of hexane. Solvent mixture (8 liters) comprising of Methanol and water in the ratio of 4:1 was passed through the layer for a period of 8 hrs at 35° C. by recycling the elluent. After 8 hrs the fenugreek bed is drained free of extracts and all the collected extracts. The collected extracts were concentrated to semisolid mass under vacuum at 50° C. The concentrated mass is re-dissolved in 5 liters of demonized water to get a clear solution. The clear aqueous solution was passed through a column containing 500 ml of strong acid cation exchange resin in macroporous form slowly over a period of 2 hrs. The column elluent were checked by TLC screening for the presence of alkaloids& amino acids. (TLC system Butanol, acetic acid, water, in the ratio 12:8:2). Detection was done using Ninhydrin reagent. After completion of the column the outlet liquid was passed through 750 ml of resin bed containing Amberlite XAD-761 over a period of 3 hours. The column remainder which is collected from the outlet is concentrated below 50° C. under vacuum to get thick paste which is spray dried in a small spray drier under following conditions.

Inlet temperature: 160° C.
Outlet temperature: 80° C.
Atomizer RPM: 12,000.

In the following examples, the test compound referred is the novel botanical compound that relates to the present invention.

The following examples were conducted to determine the effect of the novel botanical on body composition, strength and blood sugar levels.

Impaired body composition, which is defined as BMI>30 is one of the main causes and is characteristic of the pre-diabetic condition and the diabetic conditions. The following experiments reflect the property of the novel botanical compound to reduce body fat and improve body composition. In addition, an improvement in body composition by a reduction in body fat translates to an increase in muscle mass which is also the reflected by the following examples. A loss in muscle mass is a grave symptom after the onset of diabetes. The following examples also serve to reflect the ability to the novel compound in increase muscle mass. An increase in muscle mass improves body composition and reduces catabolic activities and muscle tissue breakdown associated with diabetes.

EXAMPLE 4

Effect of Test Compound of Structural Formula I on Body Composition

Immature male Wistar rats weighing about 55 gm (±5 gm) were selected for the study. These rats were anesthetized by anesthetic ether and castrated. After 4 weeks of treatment, animals were sacrificed and the seminal vesicles, the ventral prostate, and the muscle levator ani carefully dissected and weighed. Body weight of the animals was registered at the beginning and at the end of the experiment. Increase in weight of seminal vesicles and ventral prostate indicates androgenic activity, whereas increase in weight of levator ani muscles was considered to indicate anabolic activity.

Figure 3A:
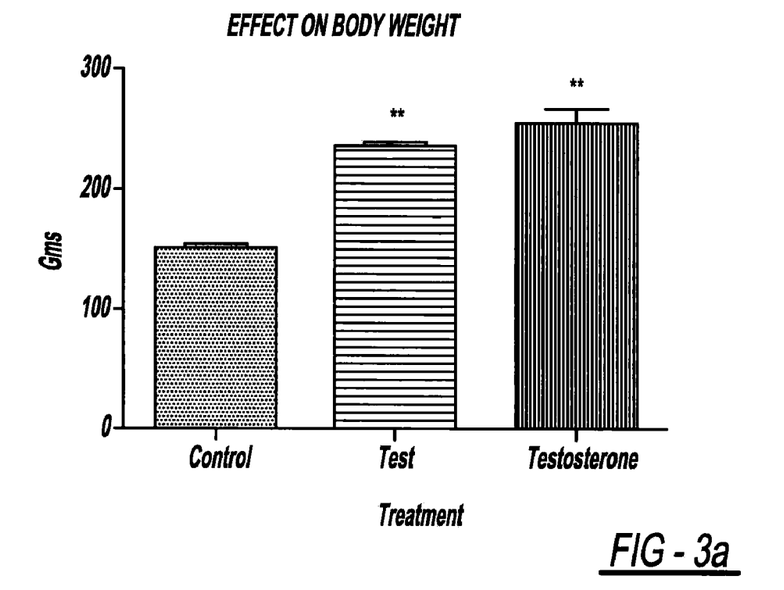
FIG. 3 are histogram charts of results obtained for the study of test compound of structural formula I on body weight.
Figure 3B:
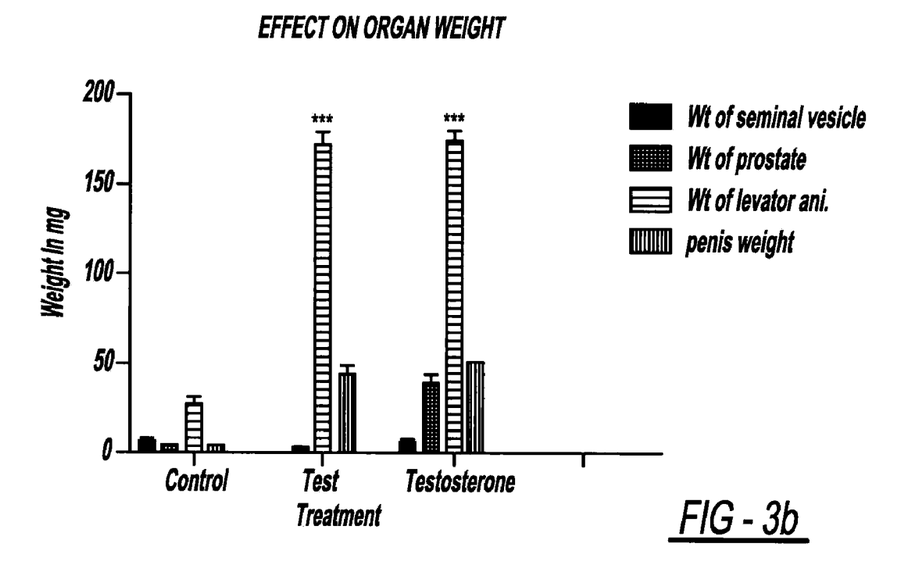

The four-week treatment with the test compound (10 mg/kg p.o) did not cause any change in the body weight of the rats while testosterone (10 mg s.c biweekly) and the test compound (35 mg/kg p.o) groups showed significant rise in body weight when compared with control group. The results of the study are provided as histogram chart in FIG. 3.

The test compound (10 and 35 mg/kg) did not increase the weights of organs of the male reproductive system i.e. prostate, seminal vesicle and penis. This important result shows that although the test compound has anabolic activity it does not have any androgenic effects on the animals. In addition, it is important to note that the test compound showed a significant increase in the weight of the levator ani muscles.

Non-Androgenic Effect of Test Compound:

In addition, to rule out any possibility of androgenic activity in the increase in body weight and muscle mass, the serum testosterone levels were measured.

Immature male Wistar rats weighing about 55 gm (±5gm) were selected for the study. These rats were anesthetized by anesthetic ether and castrated. After four weeks of treatment, the blood was withdrawn from the rats by retro orbital puncture method and analyzed for serum testosterone, which was measured with the help of radioimmunoassay (RIA) kit.

Figure 4:
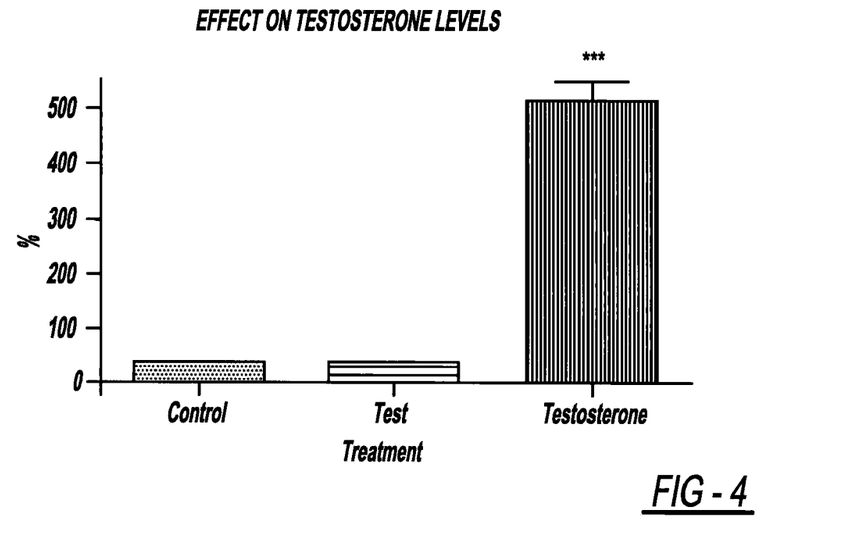
FIG. 4 is a histogram of effect on testosterone levels by test compound of structural formula I.

An important and interesting point to note is that there was no significant increase in the total serum testosterone levels seen after daily treatment with the test compound at a dose of 35 mg/kg p.o. The results of the study are provided in the form of histogram chart in FIG. 4.

EXAMPLE 5

Clinical Study to Confirm Efficacy of Test Compound

Subsequently, a double-blind, placebo-controlled study in 49 pre-trained volunteers was conducted to assess the safety and efficacy of the test compound. This 2 month study was conducted with supplementation of 500 mg of the test compound and the volunteers were on resistance training 4 times/week. During this study the effect of the test compound on body composition (fat content) and strength were evaluated.

Figure 5:
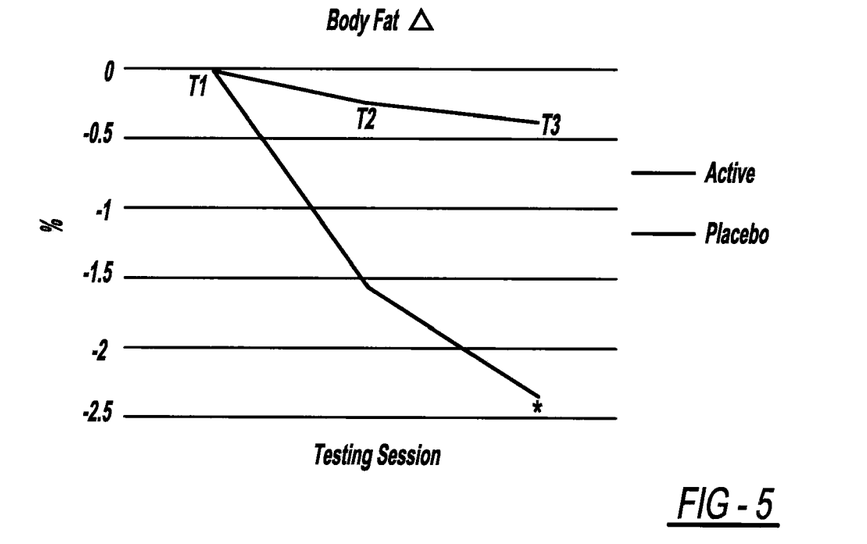
FIG. 5 is a graph showing the effect of test compound of structural formula I on body composition.

Body Composition:

Body density was analyzed by bioelectric impedance and hydrostatic weighing. Based on these parameters fat free mass was calculated. From the FIG. 5 it is concluded that during the study period of 8 weeks, the test product reduced the body fat by 12%. This is a significant reduction.

Body composition is used to describe the percentage of bone, fat and muscle in the body. Reduction in body fat with constant body weight is an indication of an increase in muscle mass. The test compound reduces body fat while maintaining body weight. Thus, the test compound increases muscle mass.

Strength:

Since this product was used to increase muscle mass, the effect of the test compound on the strength of the volunteers was evaluated. This was done by conducting isotonic repetitions of bench and leg press exercises. An increase in strength was determined based on an increase in weight lifted during these two exercises.

Figure 6A:
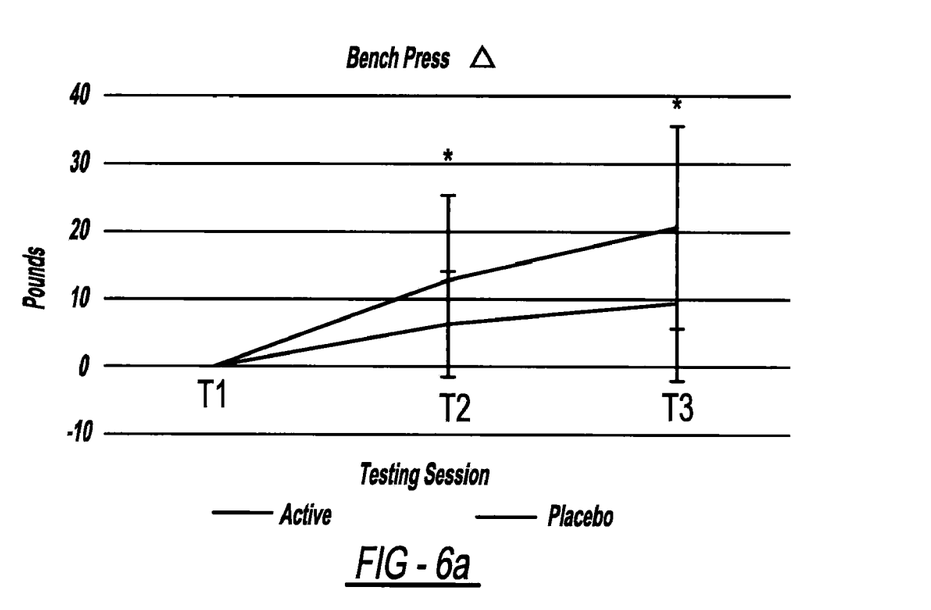
FIG. 6 is a graph showing the effect of test compound of structural formula I on strength.
Figure 6B:
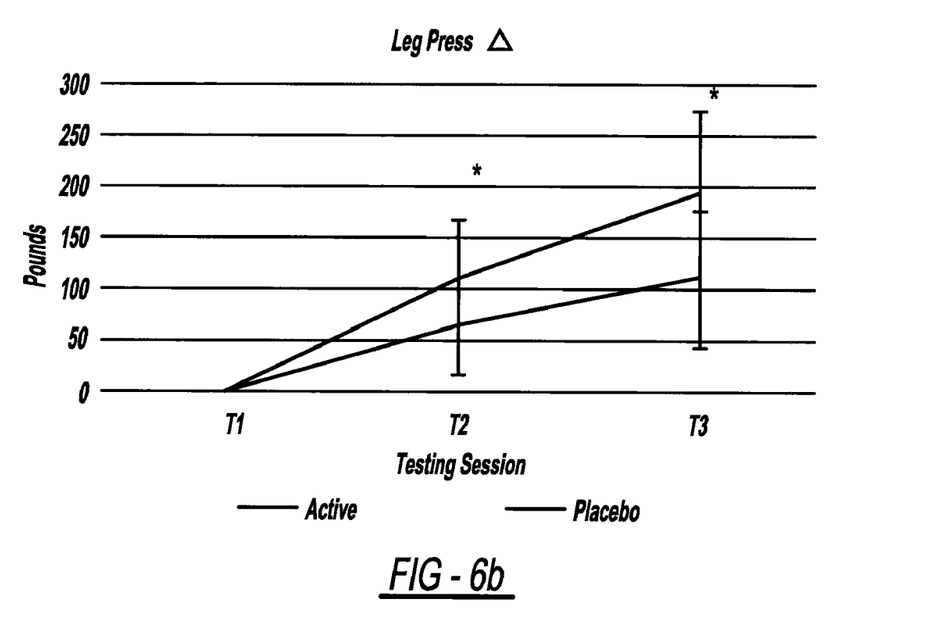

There was a significant increase in strength indicated by an increase in ability to lift weights on the bench and leg press. There was a 100% increase when compared to the placebo in the bench press and an 80% increase when compared to the placebo in the leg press exercise. This increase is statistically significant when compared to the placebo and is reflective of the efficacy of the test compound in strength enhancement. The results of this study are provided graphically in FIG. 6.

EXAMPLE 6

Ability of the Test Compound to Drive Glucose into the Cell: Insulin-Like Action This example studies the time and dose dependant uptake of Deoxy-D-Glucose, 2-(1-$^{14}$C) uptake in 3T3-L1 cells treated with the test compound.

3T3-L1 cells were cultured (DMEM+FBS) in a 24 well plate and were treated with a 5 µg/ml and a 50 µg/ml dose of the test compound for 10 or 30 min. Cells treated with 100 nM insulin was used as a positive control. Radioactivity (cpm) was measured with TopCount (Packard).

Figure 7:
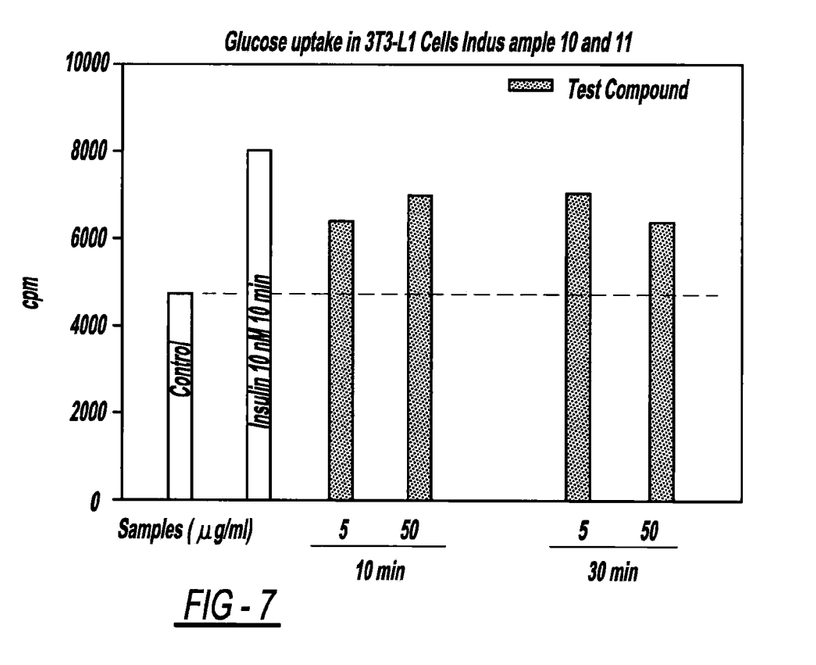
FIG. 7 is a histogram showing the ability of compound structural formula I to drive glucose into the cells.

This study showed that Insulin treatment for 10 min stimulated glucose uptake by 1.74 fold. Treating cells with the test compound resulted in an enhanced glucose uptake at a dose of 5 µg/ml. Data obtained in this study matches with the result of video imaging of GLUT4 translocation in CHO-GLUT4eGFP cells. The results of the study are provided in histogram of FIG. 7.

From the above the study the ability of the test compound to mimic an insulin-like activity and drive glucose into the cell is evident.

EXAMPLE 7

Effect of Test Compound on Blood Sugar Levels and Body Weight in the Early Stages of Diabetes Induced with Alloxan Male Wistar rats were injected with alloxan monohydrate (160 mg/kg i.p.) to induce diabetes. After 48 hours of injection blood glucose levels were determined using glucose estimation kits. Animals with blood glucose levels above 300 mg/dl were selected and divided into four groups of 6 rats in each group.

Group 1: Non-Diabetic Control
Group 2: Diabetes Control
Group 3: Test Compound (60 mg/kg)
Group 4: Pioglitazone (Standard Drug) (5 mg/kg)

The animals were given respective drug solutions in stipulated dose, for 30 days. On the $0^{th}$, $15^{th}$ and $30^{th}$ day of treatment, the blood sugar levels and body weights were analyzed.

Blood Sugar Levels:

Serum was obtained by centrifuging the blood obtained by retero-orbital blood withdrawal at 7000 rpm at 4° C. for 15 min. The serum obtained was collected for Blood sugar level determinations. The below table provides data on blood glucose levels of various groups.

The test compound treated group showed a significant reduction in blood sugar levels (55% reduction) on the $30^{th}$ day. The Pioglitozone group was used as a standard drug model. The test compound showed excellent diabetic control and ability to reduce elevated blood sugar levels.

Alloxan is an organic compound that is commonly used to experimentally induce diabetes in rats. Its effectiveness is due to its selective action on the beta cells of the pancreas in rats. Since this compound is structurally similar to glucose, and is thus taken up by the GLUT2 molecule in the beta cells of the rat pancreas. Thus, the use of alloxan enables the evaluation of beta cell protection against this compound. Beta cell damage is accompanied by an increase in blood sugar levels. Thus an indication of beta cell protection is the reduction of blood glucose levels even after treatment with alloxan.

This experiment reflects the ability of the test compound to reduce blood sugar levels even in the presence of alloxan thus reflecting the prophylactic effect on the beta cells of the pancreas.

Thus from the above experiment, it is concluded that the test compound has the ability to reduce blood sugar levels in a diabetic condition and a pre-diabetic condition. Additionally, the test compound also has a prophylactic effect against the effect of alloxan on the beta cells of the pancreas. This shows the potential of this compound to be used in both the diabetic and pre-diabetic condition.

Body Weight:

The mean body weight increased significantly in Non-diabetic rats. There was a significant decrease in body weight in diabetic group as compared to non diabetic group. In the test compound treated group the body weight on 0 day was 185.16 & 240.83 on 30 day. This study showed an increase in weight in the animals treated with the test compound. These animals also exhibited better diabetic control. There was a 29% increase in weight in the animals treated with the test compound that was an excellent result when compared to the 9% decrease in body weight of the untreated diabetic animals. The below table provides the percentage change in body weight of groups treated with respective treatments.

TABLE 1

Blood sugar levels of groups treated with compound of structural formula I and others

| Group & Treatment | Blood sugar level (mg/dl) | | | Change in BSL (%) |
|---|---|---|---|---|
| | 0 day | 15 day | 30 day | |
| Non diabetic (Vehicle) | 93.17 ± 3.53 | 103.41 ± 4.0 | 114.12 ± 3.44 | 21.5% increase |
| Diabetic control (Vehicle) | 361.66 ± 5.11 | 458.83 ± 5.34 | 502.16 ± 5.93 | 38.84% increase |
| Test Compound, structural formula I (60 mg/kg) | 416.5 ± 14.42 | 294.5 ± 12.22 | 187 ± 9.33 | 55% DECREASE |
| Fenugreek Seed Powder (2 g/kg) | 406.6 | 424.7 | 404.55 | Non significant |
| Crude Alcohol Extract of Fenugreek (1 g/kg) | 354.5 | 347.8 | 361.6 | Non significant |
| Pioglitazone (5 mg/kg) | 438.66 ± 6.37 | 376.33 ± 7.29 | 281 ± 5.92 | 35.8% DECREASE |

TABLE 2

Percentage change in body weight of groups treated
with compound of structural formula I and others

| Group & Treatment | Body weight (gm) | | | % Change in Body weight |
|---|---|---|---|---|
| | 0 day | 15 day | 30 day | |
| Non-diabetic (Vehicle) | 143.33 ± 4.43 | 209.5 ± 5.01 | 223.66 ± 4.95 | 56% INCREASE |
| Diabetic control (Vehicle) | 166.83 ± 4.88 | 158 ± 5.52 | 151.33 ± 4.92 | 9% DECREASE |
| Test Compound, Structural formula I (60 mg/kg) | 185.16 ± 6.53 | 215.83 ± 6.05 | 240.83 ± 6.42 | 29% INCREASE |
| Pioglitazone (5 mg/kg) | 165 ± 5.41 | 198.5 ± 6.45 | 207.83 ± 4.49 | 25% INCREASE |

Weight loss is one of the clinical features of diabetes and is an indication of poor diabetic control. This loss in weight is speculated to be due to the degeneration of adipocytes and muscle tissues to make up for the energy lost due to frequent urination and over-conversion of glycogen to glucose. Management of weight loss is a key feature in the management of diabetes.

Hence the test compound reflected significant potential in mitigating weight loss as well as in increasing the weight of diabetic animals.

A subsequent study was done to evaluate the impact of the increase in weight on the muscle content of the animals. This study showed that there was an increase in muscle mass, and thus the increase in weight can be attributed to an increase in muscle mass and not body fat.

The levitor ani muscles of these animals were checked for the drugs effect on muscle mass.

Figure 8:
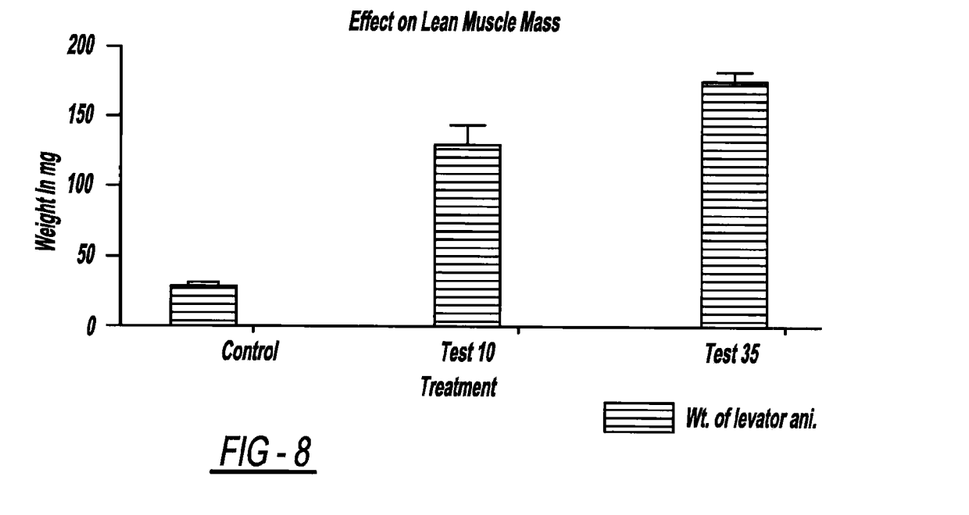
FIG. 8 is a histogram showing the effect of compound of structural formula I on Lean Muscle Mass

As seen from the graph provided as FIG. 8, there is a significant increase in muscle mass in the animals on treatment with the test compound. From the above two results it can be concluded that the test compound has a positive effect on overall body composition. Maintaining a healthy body composition is one of the key targets to control the progression of the pre-diabetic condition and to maintain.

A combination of blood glucose control (as shown above) and maintaining a healthy body composition is very important to control the progression of a preliminary pre-diabetic condition to diabetes. Additionally a control on both blood sugar levels and an improvement in body composition is important to control the diabetic disease as well. Hence the test compound is very well suited for diabetic and pre-diabetic applications.

The above description is illustrative of the various embodiments of the invention and is not to be construed as limiting, it being understood that a person skilled in the art may carry out many obvious variations to the present invention.

What is claimed is:

1. A purified compound of structural formula I

Formula I

2. The compound as claimed in claim 1, wherein said compound is a low molecular weight galactomannan having molecular weight of 702 daltons.

3. The compound as claimed in claim 1, wherein said compound has a molecular formula of $C_{24}H_{46}O_{23}$.

4. The compound as claimed in claim 1, wherein said compound is obtained from plant *Trigonella foenum graecum*.

5. The compound as claimed in claim 1, wherein said compound improves body composition, strength and factors associated with pre-diabetic and diabetic conditions, wherein said improvement of the pre-diabetic and diabetic conditions comprises a member selected from the group consisting of poor body composition, low lean muscle mass, decreased fat burning, decreased strength, impaired glucose metabolism, increased resistance to insulin, increase in blood glucose, cardiovascular diseases, obesity and type-2 diabetic condition.

6. A composition comprising purified compound of structural formula I

Formula I optionally along with pharmaceutically acceptable additive(s) for improving body composition, strength and factors associated with pre-diabetic and diabetic conditions, wherein said improvement of the pre-diabetic and diabetic conditions comprises a member selected from the group consisting of poor body composition, low lean muscle mass, decreased fat burning, decreased strength, impaired glucose metabolism, increased resistance to insulin, increase in blood glucose, cardiovascular diseases, obesity and type-2 diabetic condition.

7. The composition as claimed in claim 6, wherein the additives are selected from the group consisting of granulating agents, binding agents, lubricating agents, disintegrating agents, sweetening agents, coloring agents, flavoring agents, coating agents, plasticizers, preservatives, suspending agents, emulsifying agents and spheronization agents.

8. The composition as claimed in claim 6, wherein said composition is formulated into various dosage forms selected from the group consisting of tablet, troches, lozenges, aqueous or oily suspensions, dispersible powders or granules, emulsion in hard or soft gel capsules, syrups and elixirs.

9. The composition as claimed in claim 6, wherein said compound is obtained from plant parts of *Trigonella foenum graecum*.

10. The composition as claimed in claim 9, wherein said plant parts are selected from the group consisting of roots, shoots, leaves, and seeds.

11. The composition as claimed in claim 6, wherein said composition is non-toxic and free of side effects.

12. A process for preparation of purified compound of structural formula I

Formula I from plant *Trigonella foenum-graecum*, wherein said process comprises steps of
  a) extracting flaked seeds with aliphatic hydrocarbon solvent and hydro-alcohol to remove fatty matter to obtain an extract;
  b) concentrating the extract to obtain a semi solid mass;
  c) dissolving concentrated semi solid mass to obtain a clear solution;
  d) passing the clear solution through ion-exchange resin to remove nitrogenous and ionic bases to obtain a clarified solution;
  e) passing the clarified solution through an adsorbent column to obtain a resultant clear solution; and
  f) concentrating the resultant clear solution followed by drying under vacuum to obtain powder of the compound of formula I.

13. The process as claimed in claim 12, wherein said extraction is carried out for a time period ranging from about 3 hr to about 12 hr.

14. The process as claimed in claim 12, wherein said extraction is carried out at a temperature ranging from 30 to 40° C.

15. The process as claimed in claim 12, wherein said aliphatic hydrocarbon solvent is selected from the group consisting of hexane, heptane, octanes and cyclohexanes.

16. The process as claimed in claim 12, wherein the hydro alcohol for extraction is in a ratio ranging from 1:9 to 9:1.

17. The process as claimed in claim 12, wherein said extract is concentrated under vacuum at a temperature ranging from about 45° C. to about 55° C.

18. The process as claimed in claim 12, wherein said mass is dissolved in deionized water.

19. The process as claimed in claim 12, wherein said ion-exchange resin is cation exchange gel type resin.

20. The process as claimed in claim 12, wherein the yield of the compound of formula I is about 32 g/1000 g of fenugreek seeds.

21. The process as claimed in claim 12, wherein the purity of the compound of formula I is ranging from 90% to 97%.

22. The process as claimed in claim 12, wherein said extract is concentrated under vacuum at a temperature ranging from 50 to 75° C.

23. A method of treating pre-diabetic and diabetic disease conditions in a subject in need thereof, said method comprising step of administering pharmaceutically effective amount of purified compound of structural formula I Formula I optionally along with pharmaceutically acceptable additives to the subject.

24. The method of treating as claimed in claim 23, wherein said pre-diabetic and diabetic conditions comprises poor body composition, low lean muscle mass, decreased fat burning, decreased strength, impaired glucose metabolism, increased resistance to insulin, increase in blood glucose, cardiovascular diseases, obesity and type-2 diabetic condition.

25. The method of treating as claimed in claim 23, wherein said additives are selected from the group consisting of granulating agents, binding agents, lubricating agents, disintegrating agents, sweetening agents, coloring agents, flavoring agents, coating agents, plasticizers, preservatives, suspending agents, emulsifying agents and spheronization agents.

26. The method of treating as claimed in claim 23, wherein said composition is formulated into various dosage forms selected from the group consisting of tablet, troches, lozenges, aqueous or oily suspensions, dispersible powders or granules, emulsion in hard or soft gel capsules, syrups and elixirs.

27. The method of treating as claimed in claim 23, wherein the subject is an animal or human being.

28. The method of treating as claimed in claim 23, wherein said compound improves pre-diabetic and diabetic conditions comprising poor body composition, low lean muscle mass, decreased fat burning, decreased strength, impaired glucose metabolism, increased resistance to insulin, increase in blood glucose, cardiovascular diseases, obesity and type-2 diabetic condition.

29. The method of treating as claimed in claim 23, wherein said compound is obtained from plant parts of *Trigonella foenum graecum*.

30. The method of treating as claimed in claim 29, wherein said compound is obtained from plant parts selected from the group consisting of roots, shoots, leaves, and seeds.

* * * * *